US005545198A

United States Patent [19]
Owens

[11] Patent Number: 5,545,198
[45] Date of Patent: Aug. 13, 1996

[54] METHOD OF HEATING SEAT CUSHION WITH REMOVABLE HEATING PAD

[75] Inventor: Bryon C. Owens, Asheboro, N.C.

[73] Assignee: Vesture Corporation, Asheboro, N.C.

[21] Appl. No.: 533,180

[22] Filed: Sep. 25, 1995

Related U.S. Application Data

[63] Continuation of Ser. No. 224,552, Apr. 7, 1994, abandoned, which is a continuation-in-part of Ser. No. 136,021, Oct. 14, 1993, Pat. No. 5,500,010, which is a continuation of Ser. No. 85,570, Jun. 30, 1993, Pat. No. 5,300,105, which is a continuation of Ser. No. 871,826, Apr. 21, 1992, abandoned, which is a continuation of Ser. No. 643,344, Jan. 22, 1991, abandoned, which is a continuation-in-part of Ser. No. 486,806, Feb. 26, 1990, abandoned.

[51] Int. Cl.[6] ..................................... A61F 7/00
[52] U.S. Cl. ................ 607/108; 607/112; 607/114
[58] Field of Search ............... 607/96, 104, 108–112, 607/114

[56] References Cited

U.S. PATENT DOCUMENTS

| | | |
|---|---|---|
| 1,927,751 | 9/1933 | Mensi . |
| 2,203,591 | 6/1940 | Brown . |
| 2,438,643 | 3/1948 | Moore . |
| 2,488,964 | 11/1949 | Conrad .................................. 607/96 X |
| 2,515,298 | 7/1950 | Fledman . |
| 2,675,630 | 4/1954 | Youmans . |
| 3,014,117 | 12/1961 | Madding ............................ 607/114 X |
| 3,082,611 | 3/1963 | Alvis et al. . |
| 3,521,310 | 7/1970 | Greenawalt . |
| 3,611,455 | 10/1971 | Gottfried . |
| 3,738,702 | 6/1973 | Jacobs ................................ 607/104 X |
| 3,872,525 | 3/1975 | Lea et al. ..................................... 5/348 |
| 3,885,403 | 5/1975 | Spencer ..................................... 62/530 |
| 3,893,834 | 7/1975 | Armstrong .......................... 607/114 X |
| 4,123,855 | 11/1978 | Thedford . |
| 4,249,319 | 2/1981 | Yoshida . |
| 4,283,427 | 8/1981 | Winters et al. . |
| 4,425,917 | 1/1984 | Kuznetz ................................... 128/403 |
| 4,488,552 | 12/1984 | McCann et al. ......................... 128/402 |
| 4,499,131 | 2/1985 | Knox ........................................... 428/68 |
| 4,573,447 | 3/1986 | Thrash et al. ........................ 607/114 X |
| 4,580,393 | 4/1986 | Furukawa ..................................... 3/512 |
| 4,604,987 | 8/1986 | Keltner . |
| 4,671,267 | 6/1987 | Stout ...................................... 128/156 |
| 4,694,829 | 9/1987 | Frye ......................................... 607/114 |
| 4,743,726 | 5/1988 | Hughes et al. . |
| 4,756,311 | 7/1988 | Francis, Jr. . |
| 4,821,354 | 4/1989 | Little .................................... 607/104 X |
| 4,841,646 | 6/1989 | Maurer, Jr. . |
| 4,849,593 | 7/1989 | Hughes et al. . |
| 4,868,898 | 9/1989 | Seto ..................................... 607/108 X |
| 4,914,717 | 4/1990 | Gibbon . |
| 4,920,964 | 5/1990 | Francis, Jr. .............................. 607/114 |
| 4,931,608 | 6/1990 | Bills . |
| 4,933,193 | 6/1990 | Fisher . |
| 4,942,634 | 7/1990 | Saloff et al. . |
| 4,983,798 | 1/1991 | Eckler et al. . |
| 5,035,241 | 7/1991 | Walasek et al. ......................... 128/403 |
| 5,038,779 | 8/1991 | Barry et al. .............................. 128/402 |
| 5,050,598 | 9/1991 | Tucker . |

(List continued on next page.)

OTHER PUBLICATIONS

Prior art pad.
Therapeutic pad shown in FIGS. 1–5 of pending patent application Ser. No. 08/224,569, filed 7 Apr. 1994.

*Primary Examiner*—Angela D. Sykes
*Assistant Examiner*—Bryan K. Yarnell

[57] ABSTRACT

A microwavable heating pad has a liquid absorbent to prevent liquid leakage in the event the sealed thermoplastic envelope of the pad is ruptured. The method of forming the pad includes evacuating the air from the thermoplastic envelope prior to sealing. The heating pad is used conjunction with a special seat cushion for outdoor events, such as football games, where a user must sit relatively inactive for an extended period of time. The seat cushion comprises an inner pocket to centralize the heating pad within the seat cushion and also includes a back rest and a front pouch that can be fastened together to hold the heated seat cushion in a neat, compact configuration during storage or transportation.

21 Claims, 8 Drawing Sheets

U.S. PATENT DOCUMENTS

| | | | |
|---|---|---|---|
| 5,052,369 | 10/1991 | Johnson | 126/400 |
| 5,070,233 | 12/1991 | Colasante . | |
| 5,094,238 | 3/1992 | Gibbon | 128/403 |
| 5,150,707 | 9/1992 | Anderson | 128/402 |
| 5,230,170 | 7/1993 | Dahle . | |
| 5,230,333 | 7/1993 | Yates et al. . | |
| 5,259,379 | 11/1993 | Kim et al. | 607/104 |
| 5,277,180 | 1/1994 | Angelillo et al. . | |
| 5,300,105 | 4/1994 | Owens . | |
| 5,331,688 | 7/1994 | Kiyohara . | |
| 5,339,541 | 8/1994 | Owens . | |
| 5,357,693 | 10/1994 | Owens . | |
| 5,366,491 | 11/1994 | Ingram et al. . | |
| 5,561,441 | 12/1985 | Kolodziej | 607/114 |

METHOD OF HEATING SEAT CUSHION WITH REMOVABLE HEATING PAD

This is a file wrapper continuation of application Ser. No. 08/224,552 filed 7 Apr. 1994, now abandoned, which was a continuation-in-part of application Ser. No. 08/136,021, now U.S. Pat No. 5,500,010, filed 14 Oct. 1993, which was a continuation of application Ser. No. 08/085,570 filed 30 Jun. 1993, now U.S. Pat. No. 5,300,105, which was a continuation of Ser. No. 07/871,826 filed 21 Apr. 1992 now abandoned, which was a continuation of Ser. No. 07/643,344 filed 22 Jan. 1991 now abandoned, which was a continuation-in-part of Ser. No. 07/486,806 filed 26 Feb. 1990 now abandoned.

BACKGROUND OF THE INVENTION

1. Field of the Invention

The invention herein pertains to heated seat cushions and particularly pertains to a heated seat cushion having a removable, microwavable heating pad.

2. Description of the Related Art and Objectives of the Invention

It is well known that liquid-containing heating pads are designed to heat parts of the human body to help heal injuries, alleviate soreness, and provide comfort in cold environments. Heating pads may be conventional hot water bottles, which can be filled with heated liquid, or may be modern, sealed liquid pouches, which can be microwaved and then used for heating purposes. In recent years, heating pads that consist of flexible plastic envelopes containing water-type solutions have been manufactured and sold. Such pads are manufactured by placing them in a vacuum pump and evacuating the air within the envelopes. The envelopes are then heat sealed with the liquid therein. While conventional, hot water bottle types of heating pads tend to lose their heat relatively quickly, modern microwavable heating pads tend to retain heat for up to several hours, depending on their design. Also, conventional pads containing liquids for heating, which have been used in the past, are susceptible to breaking and rupturing; consequently, users' clothes, furniture, bed sheets, and the like can be damaged, requiring cleaning or even disposal. Adults are greatly concerned that small children may use heating pads that leak; accordingly, this fear has deterred the use of conventional heating pads to some degree.

Portable seat cushions are popular accessories for concert spectators, sports fans, campers, fishermen, and outdoor enthusiasts in general. Heating pads have recently been installed inside seat cushions to keep spectators and the like warm when using the seat cushions in cold conditions. However, a typical prior art seat cushion does not provide a heating pad that is removable for easy heating in a microwave oven, but instead requires that the entire seat cushion be inserted into the microwave to heat the internal pad. The heating pads in prior art seat cushions often do not remain in the centers of the cushions, which is where the heating pads function most effectively. Prior art seat cushions often do not provide convenient means to carry the cushions and often do not conveniently fold into compact, easily transported configurations. Convenient storage space for small items such as keys and money is often at a premium when a person is outdoors at a ball game, for example, using a seat cushion. Prior art seat cushions do nothing to alleviate this problem. A comfortable back rest is also often lacking in prior art seat cushions.

Thus, with the known problems and disadvantages associated with prior art heating pads, the present invention was conceived, and one if its objectives is to provide a heating pad that is constructed to prevent leaks in the event that the outer envelope is ruptured.

It is yet another objective of the present invention to provide a heating pad and a method for forming the same in which the pad has a liquid absorbent and a liquid in an envelope, which, in the event of seal breakage, will be absorbed by the liquid absorbent and will remain substantially within the envelope.

It is yet another objective of the present invention to provide a heating pad that is vacuum formed and that contains a liquid absorbent in a resilient, compressed state and a liquid.

It is yet another objective of the present invention to provide a method for easily forming a heating pad having an improved moisture impervious covering, which, in the event of pad rupture, will aid in preventing damage to clothing, bed sheets, or other materials against which it is placed.

It is also an objective of the present invention to provide a therapeutic pad that includes a readily visible temperature indication device, which will provide additional safety and efficiency in heating the pad.

Another objective of the present invention is to provide a heated seat cushion containing the microwavable heating pad of the invention for use by spectators and others who sit outside during cold weather.

Still another objective of the present invention is to provide a heated seat cushion having a microwavable heating pad that can be removed from the seat cushion.

Yet another objective of the present invention is to provide a heated seat cushion that has means to keep a heating pad centered inside the seat cushion.

Another objective of the present invention is to provide a heated seat cushion that folds into an easily transportable configuration.

Still another objective of the present invention is to provide a heated seat cushion that includes storage space for small items and a back rest for additional comfort.

Various other objectives and advantages of the present invention will become apparent to those skilled in the art as a more detailed description of the embodiments is presented below.

SUMMARY OF THE INVENTION

In view of the aforesaid objectives, the invention herein provides a new and improved heating pad, which solves many problems of conventional heating pads and other items that are now being used. The heating pad of the invention is formed from a permanently sealed, thin, flexible outer envelope, and included therein is a liquid-filled absorbent, such as a synthetic sponge, which is compressed prior to envelope sealing. The compressed sponge retains the liquid, and, in the event that the envelope is accidentally ruptured, the sponge rapidly enlarges in size, preventing any liquid within the pouch from escaping through the rupture. The method of forming the heating pad consists of placing a liquid-containing thermoplastic envelope in a vacuum chamber apparatus. A sponge is inserted into the liquid; thereafter, air is evacuated from the envelope by the use of a vacuum pump, the sponge being compressed as the envelope deflates. Once a sufficient vacuum of, for example, 24 inches of mercury is pulled, the envelope is sealed by a pair of heating elements. The sealed envelope is placed in a water impervious envelope having a rubberized covering to increase safety and durability. A thermochromic liquid crystal temperature indication device is affixed to the outer surface of the rubberized covering to indicate when the interior liquid has reached a sufficient temperature. The heating pad is then ready to be placed in a fabric cover and microwaved or otherwise heated prior to use.

The invention herein also provides a heated seat cushion that removably contains the microwavable heating pad described above. The heated seat cushion has a seat'rest with top and bottom fabric layers that house two foam blocks with the microwavable heating pad sandwiched therebetween. A zipper along the back end of the seat rest allows the heating pad to be removed for heating in a microwave oven. The foam blocks can also be removed to aid in cleaning the seat cushion. One embodiment of the seat cushion provides a shoulder strap for easy transport. Another embodiment of the seat cushion provides an inner pocket between the foam blocks to keep the heating pad centered in the seat rest between the foam blocks. This second embodiment also includes a pouch attached to the front of the seat rest for holding small items and a back rest attached to the back of the seat rest for additional comfort. The front pouch and back rest can both fold against the top of the seat rest and fasten together to provide a compact configuration for transporting and storing the seat cushion.

DESCRIPTION OF THE PREFERRED EMBODIMENT

Figure 2:
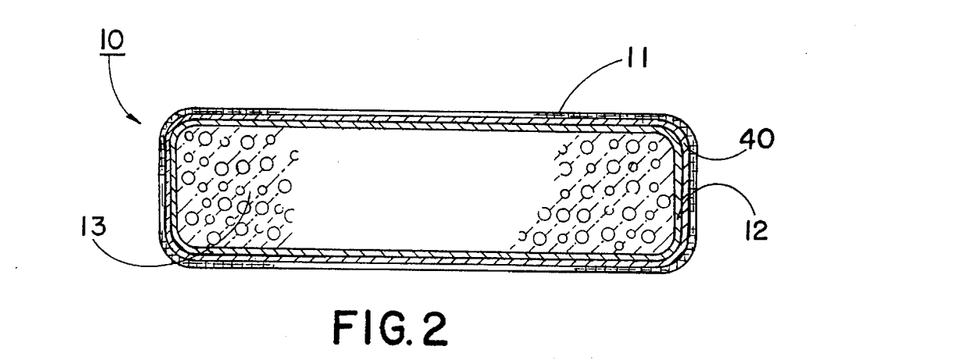
FIG. 2 demonstrates a cross-sectional view of the heating pad shown in FIG. 1 along lines 2—2.

The preferred form of the heating pad of the invention is shown in cross-sectional view in FIG. 2 and includes a fabric outer cover and a thermoplastic envelope, which contains a liquid filled sponge that has been compressed to approximately forty percent of its original size. This sponge compression allows the sponge to expand, in the event of envelope rupture, to absorb any liquid that would otherwise drain through the rupture possibly irritating or burning a user's skin or staining clothing or the like. The preferred method of forming the heating pad includes placing a flexible thermoplastic envelope containing a liquid and a sponge in a conventional vacuum-forming and heat-sealing cabinet. Upon activating the vacuum device, air is evacuated from the envelope; consequently, the envelope collapses and the sponge is compressed. Heat sealing elements then permanently seal the envelope prior to it being placed in a rubberized covering and an exterior fabric cover. The heating pad can be heated in a microwave oven, after which the heating pad will emit heat for several hours.

The preferred form of the heated seat cushion of the invention includes the microwavable heating pad described above placed between planar foam blocks in a seat rest. The seat cushion also includes a foam filled back rest attached to the back end of the seat rest for additional comfort and a front pouch attached to the front end of the seat rest to hold valuables. The front pouch and the back rest have hook and loop fasteners to hold the seat cushion in a folded, compact configuration for storage or carrying. The seat rest includes an inner pocket extending between the foam blocks for centralizing the heating pad inside the seat rest. The seat rest and the back rest both have zippers for easy removal of the foam blocks when cleaning is required. The heated seat cushion can be used at outdoor events, such as ball games or concerts, where a user must sit for an extended period of time to provide several hours of warmth.

DETAILED DESCRIPTION OF THE DRAWINGS AND OPERATION OF THE INVENTION

Figure 1:
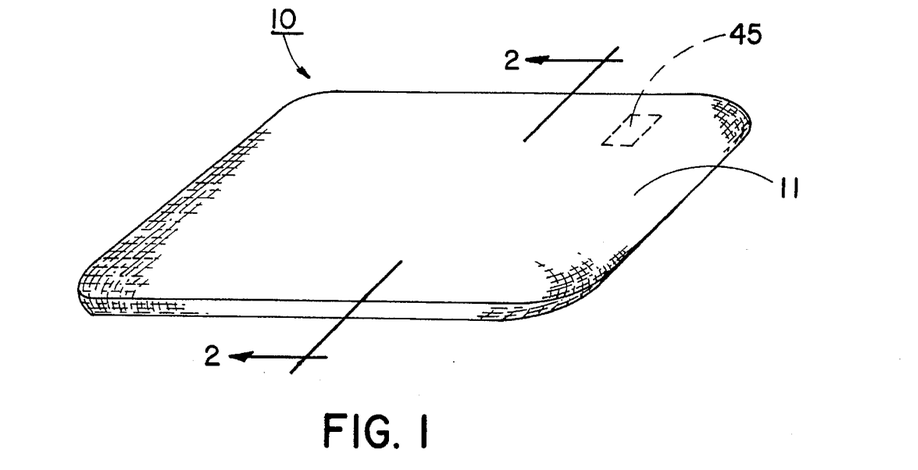
FIG. 1 illustrates an exterior perspective view of a typical heating pad of the invention.
Figure 3:
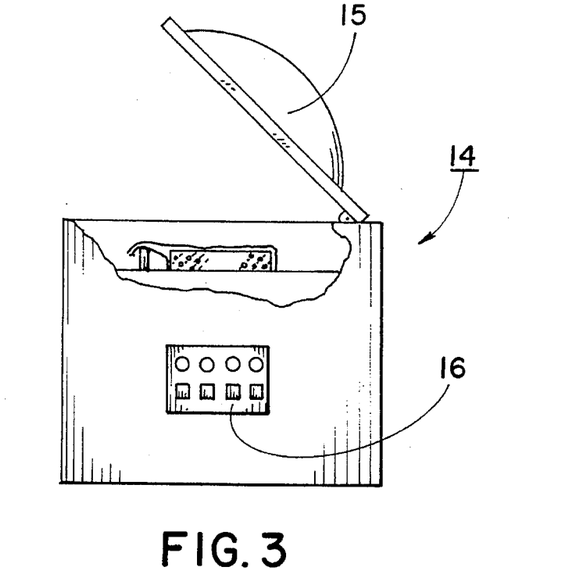
FIG. 3 pictures a conventional combination vacuum-forming and heat-sealing unit.

Turning now to the drawings, heating pad 10, as shown in FIG. 1, contains a liquid-filled microwavable pad. Heating pad 10 can be placed in a conventional microwave oven and heated for approximately five minutes. Heating pad 10 may then be removed and used as a long-lasting therapeutic heat source for a user's comfort or heat therapy. Heating pad 10 can also be used as a cooling pad by chilling it for several hours in a refrigerator or freezer prior to use for cold therapy. Heating pad 10 is shown in FIG. 2 in a cross-sectional view, whereby cover 11 is formed from a cotton fabric and encloses sealed, flexible plastic envelope 12, which may be, for example, formed from polyethylene or other suitable, durable plastics. Means 13 to absorb liquid is positioned within envelope 12 in a compressed state, as will be hereinafter explained. Means 13 may consist of a synthetic nylon sponge; however, other resilient, compressible absorbents, such as natural sponges or other synthetic or natural structures, may also be used. As seen in FIG. 2, absorbent means 13 is compressed to approximately forty percent of its normal size; as is understood, if envelope 12 is ruptured, means 13 will attempt to recover to its normal, non-compressed configuration. Water impervious covering 40 is shown in FIGS. 2 and 3 and may consist of cotton flannel rubberized sheathing, neoprene coated nylon sheeting, natural rubberized sheeting, or other similar combinations. These materials are conventional and are commonly used in hospitals and for incontinence uses on beds, chairs, and other articles. Their durability and high resistance to tearing and puncturing make them desirable; consequently, they have been found to provide superior water impervious coatings for heating pads.

Figure 4A:
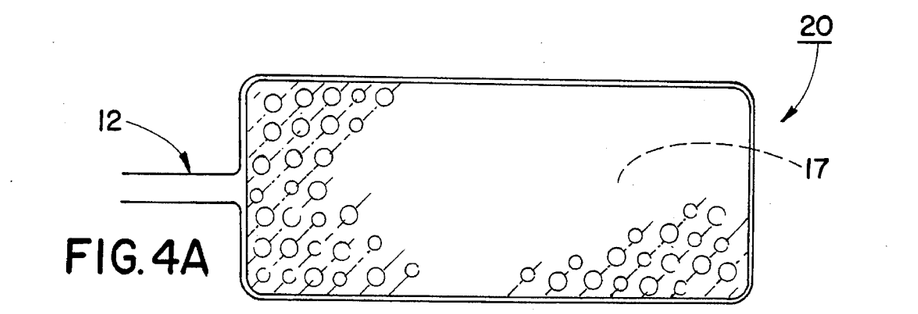
FIG. 4A depicts the envelope of the heating pad having a liquid and a liquid absorbent therein prior to vacuuming.
Figure 4B:
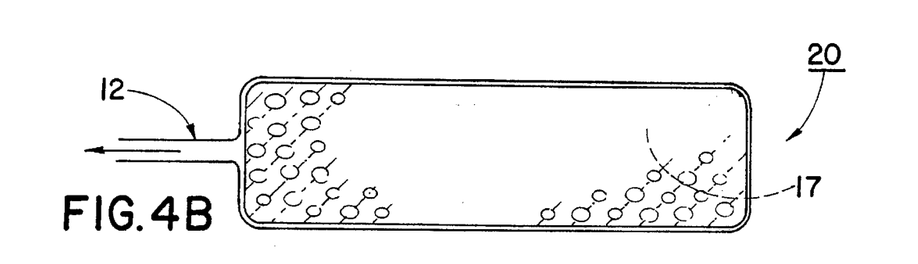
FIG. 4B illustrates the envelope of FIG. 4A but with a partial vacuum applied.
Figure 4C:
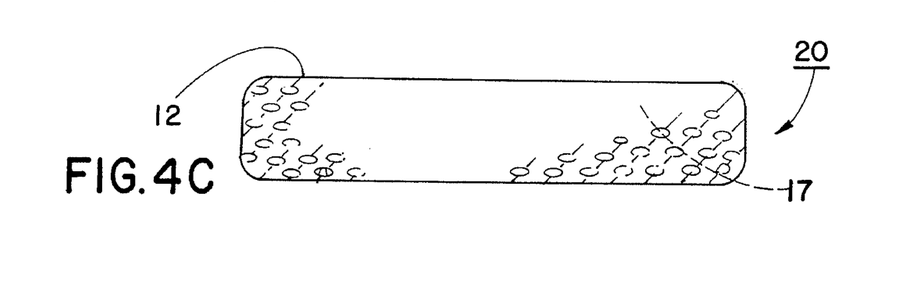
FIG. 4C shows the envelope that has been fully vacuumed and sealed prior to insertion into a rubberized covering.
Figure 5:
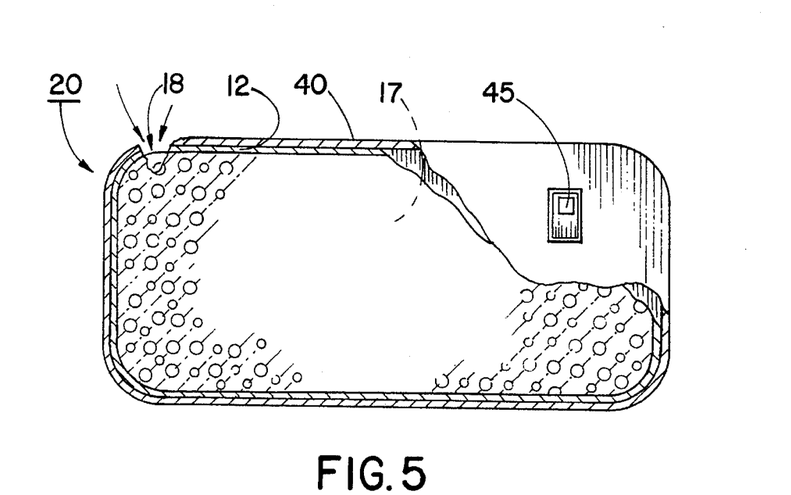
FIG. 5 illustrates the expansion of the liquid absorbent in the event of a leak in the envelope.

In FIG. 3, combination vacuum and heat sealing device 14 is shown having chamber lid 15 and control panel 16 for vacuum forming and heat sealing thermoplastic envelopes, such as envelope 12 shown in FIG. 2. Device 14 is conventional and is sold throughout the food industry for vacuum packaging meats and other products. To form a heating pad presented herein, empty envelope 12 is filled with a suitable amount of liquid, such as a water solution or a proprietary formula, and sponge 17, as shown in FIG. 4A, is placed therein. As shown in FIGS. 4B and 4C, sponge 17 is reduced in size upon evacuation of air from collapsing envelope 12, and, as pictured in FIG. 4C, sponge 17 is substantially compressed once the vacuum pressure reaches the controlled level of, for example, 24 inches of mercury. Envelope 12 is then permanently heat sealed to maintain sponge 17 in this compressed state. Thereafter, cover 11 can be applied to envelope 12 as desired. In the event that the seal of envelope 12 is broken or in the event that envelope 12 is ruptured at some surface point, air, as depicted by the arrow in FIG. 5, will rush into envelope 12 and cause sponge 17 to expand and close off rupture 18 while absorbing any liquid that may attempt to drain therethrough. Hence, with this rupture protection, heating pad 20, which contains sponge 17, is safe for use because it will not injure children or substantially damage or stain clothes, bed linens, or the like. Water impervious, rubberized covering 40 is shown in FIG. 5 surrounding envelope 12 to provide a more durable heating pad 20. Rubberized covering 40 may be formed from cotton flannel that is bonded to natural or synthetic rubber or may consist of neoprene coated nylon sheathing, which is well known in the in the incontinence product art. Also in FIG. 5, thermochromic liquid crystal temperature indicator 45 is shown positioned atop heating pad 20. Thermochromic liquid crystal temperature indicating devices are old and have been used for many years to indicate temperatures and temperature changes. Temperature indicator 45 is affixed by an adhesive or by other means to rubberized covering 40 to help a user determine the temperature of heating pad 20 and the time required to bring heating pad 20 to its desired temperature in a microwave oven.

Figure 10:
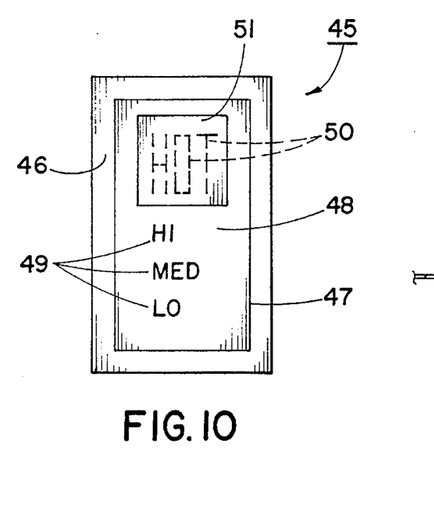
FIG. 10 pictures an enlarged view of a typical temperature indication device having temperature indicators, as used on the heating pad of the invention, in a top plan view.
Figure 11:
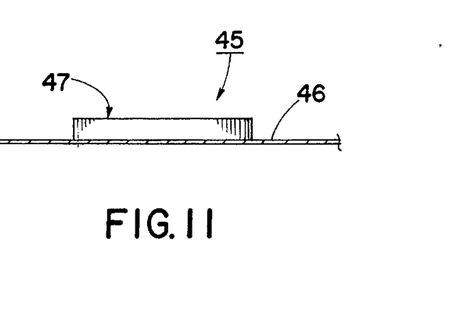
FIG. 11 depicts the temperature indication device of FIG. 10 in an end elevational view.

As seen in FIGS. 10 and 11, thermochromic liquid crystal temperature indicator 45 includes transparent, adhesive-backed base 46 for attachment to covering 40. Affixed to base 46 is polymer pouch 47, which contains liquid crystals. Various temperature indicators are available, and, as shown in FIG. 10, pouch 47 includes background top surface 48, which is black at room temperature, with white letters 49 that indicate high, medium and low temperatures. Red background 51 is shown at the top of pouch 47 with ghost letters 50 spelling "HOT" contained therein. Thus, when room temperature heating pad 20 is first placed in a microwave oven, letters 49 are white, and, as the temperature of heating pad 20 increases, the letters "LO," "MED," and "HI" sequentially change color from white to red. Also, background 51, which is red at room temperature, turns white upon sufficient heating, thereby allowing ghost letters 50 to become very apparent as they turn a solid dark red color. At this point heating pad 20 has reached its desired temperature level and may be removed from the microwave oven for use.

Figure 8:
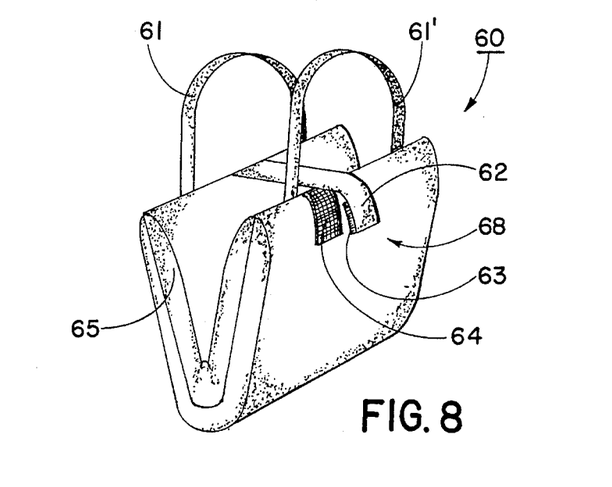
FIG. 8 depicts a foldable seat cushion containing the heating pad within.
Figure 9:
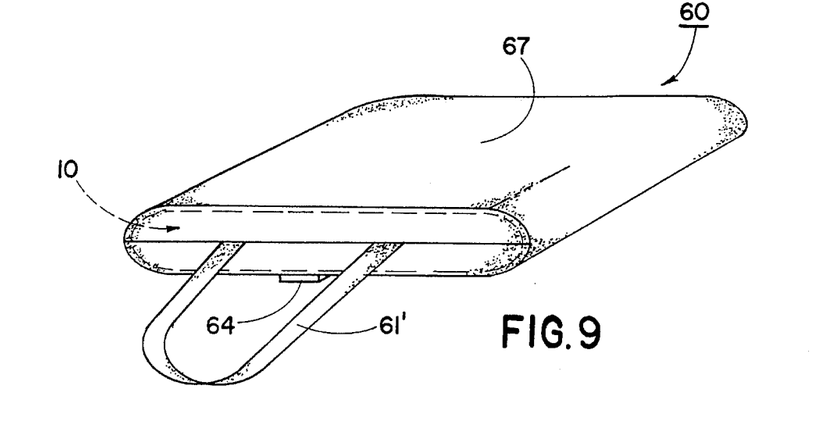
FIG. 9 shows the seat cushion of FIG. 8 in perspective view unfolded.

In FIGS. 8 and 9, heated seat cushion 60 is shown comprising a durable outer fabric or other suitable cover 67 having handles 61, 61' joined thereto. Heated seat cushion 60 can be folded closed, as shown in FIG. 8, and latched with closure strap 62 having distal end hook fastener 63 for engaging loop fastener 64, which is affixed on side 68 of heated seat cushion 60. Heated seat cushion 60 contains heating pad 10 (not seen) inside cover 67. Thus, cushion 60 can be placed in a microwave oven and heated to a desired temperature prior to use.

Figure 6:
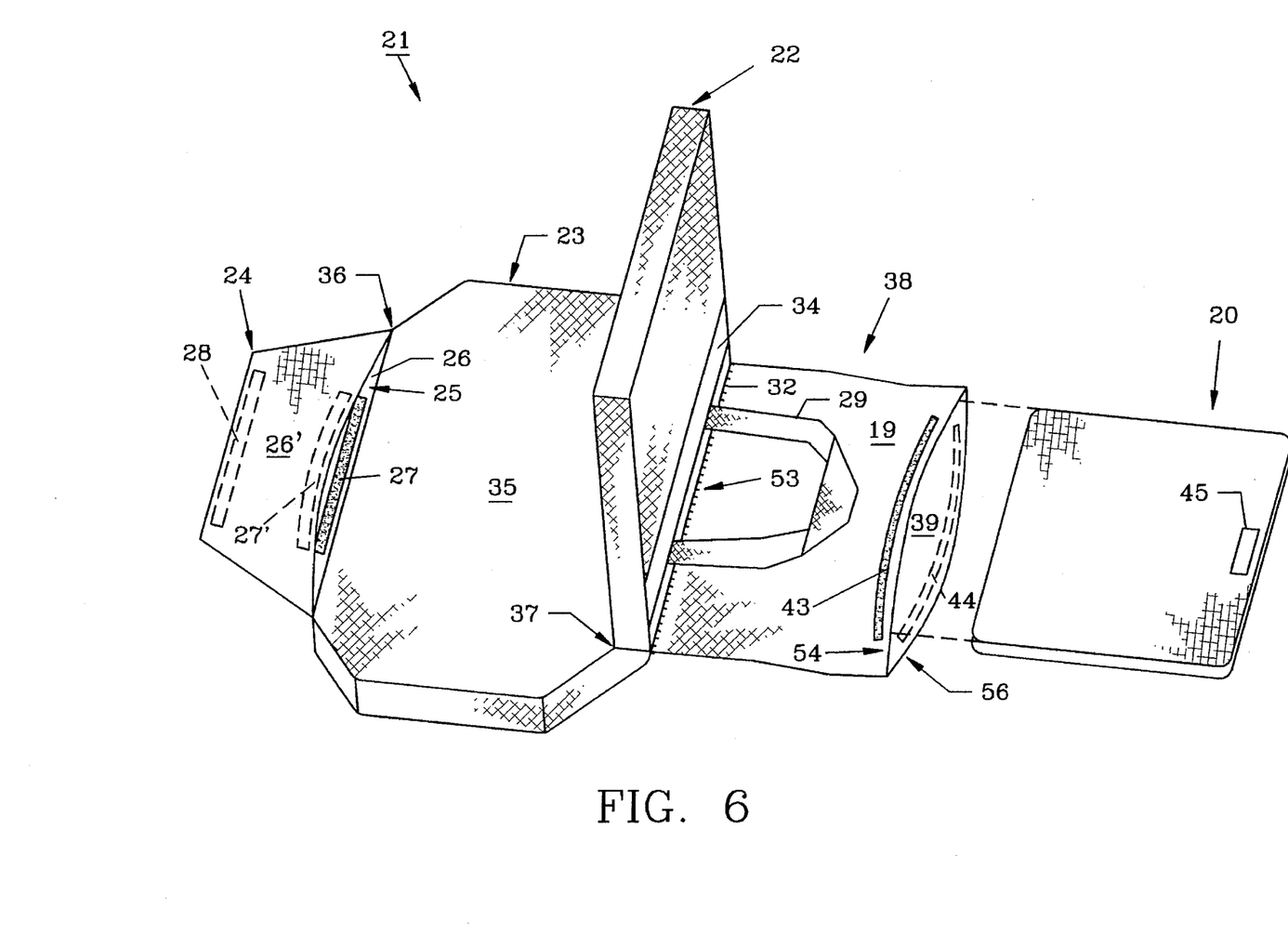
FIG. 6 shows the preferred embodiment of the heated seat cushion having a back rest, a front pouch, and an inner pocket, which has been pulled out of the seat rest, unfolded in perspective view.

The preferred embodiment, heated seat cushion 21, is shown in perspective view in FIG. 6 unfolded and disassembled. Heated seat cushion 21 includes seat rest 23 with front pouch 24 attached at the front end 36 of seat rest 23 and back rest 22 attached at the back end 37 of seat rest 23. Front pouch 24 conveniently holds a cushion user's keys, money, snacks or other small items. Front pouch 23 has first wall 26, which is attached to seat rest 23, and second wall 26', which is not attached to seat rest 23, thus creating pouch opening 25. To prevent loss of the user's valuables, a means is provided to close pouch opening 25, such as hook and loop fasteners 27, 27'. Pouch closure hook fastener 27 is attached inside front pouch 24 to first wall 26, proximate pouch opening 25; likewise, pouch closure loop fastener 27' is attached inside front pouch 24 to second wall 26', proximate pouch opening 25 and facing pouch closure hook fastener 27. Heated seat cushion 21 is covered by a suitable durable fabric or other material; for example, top fabric cover layer 35 of seat rest 23 is composed of a Teflon® treated nylon fabric to resist stains and repel dirt yet remain comfortable and breathable. Both back rest 22 and front pouch 24 likewise comprise the same outer material as top fabric cover layer 35 of seat rest 23.

Figure 12:
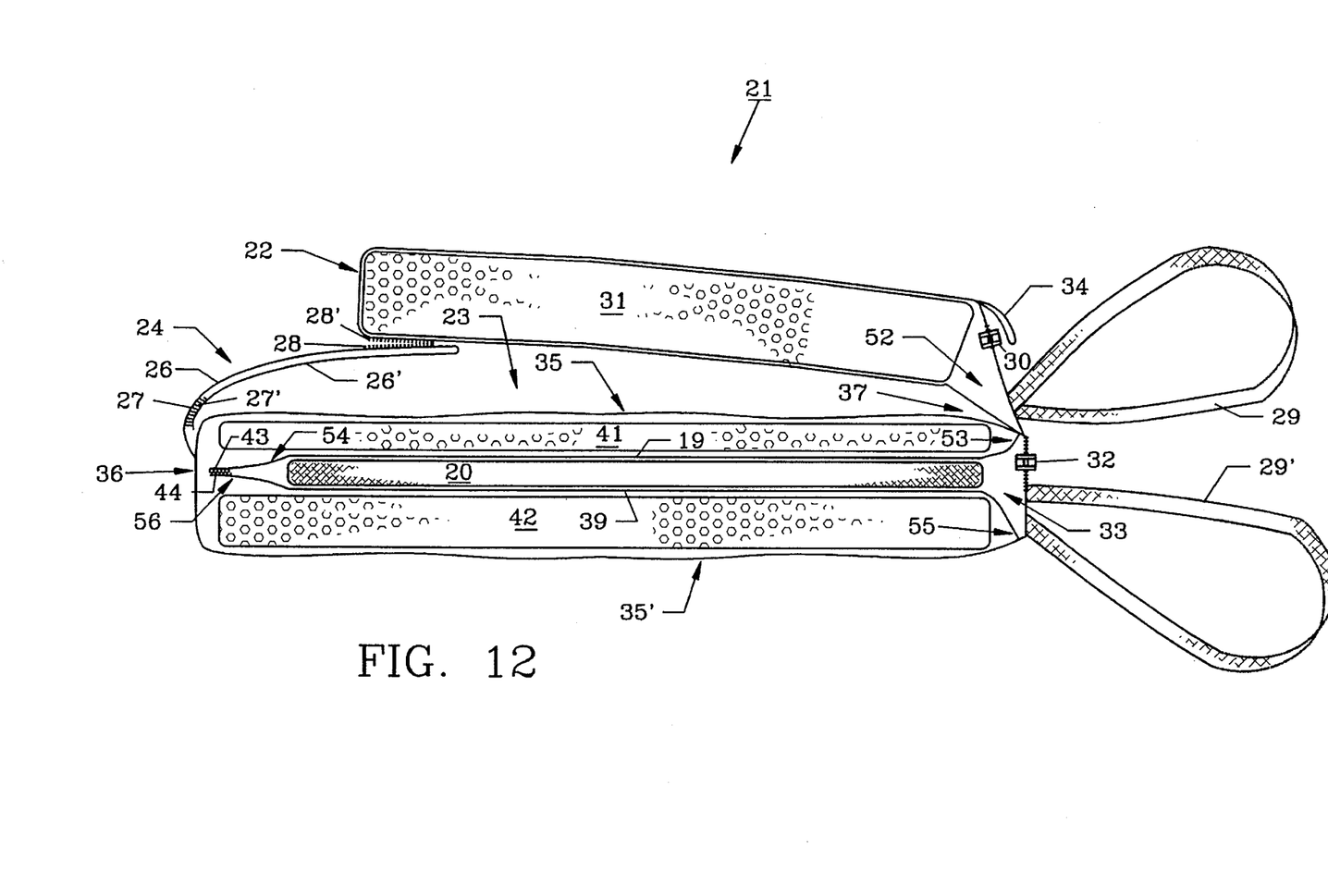
FIG. 12 shows a schematic cross-sectional view of the heated seat cushion in a folded configuration, as seen along lines 12—12 of FIG. 7.

FIG. 12 shows a schematic cross-sectional side view of folded heated seat cushion 21 revealing its internal structure. Front pouch 24 is folded over seat rest 23 and back rest 22 is folded over first wall 26. A means, such as hook and loop fasteners 28, 28', is provided to keep heated seat cushion 21 closed when it is folded for storage or transport. Seat cushion closure hook fastener 28 is attached to front pouch 24 near the distal end of first wall 26, and seat cushion closure loop fastener 28' is correspondingly attached to back rest 22 in such a position that heated seat cushion 21 can be folded closed and kept closed by mating seat cushion closure hook and loop fasteners 28, 28'.

Seat rest 23 is covered by top and bottom fabric cover layers 35, 35', as previously described, which define inner compartment 33. Access to inner compartment 33 is provided by a means to open and close inner compartment 33 such as zipper 32. Inner compartment contains top planar, resilient foam block 41 and bottom planar, resilient foam block 42, which is approximately twice as thick as top foam block 41. Seat inner pocket 38, which comprises upper layer 19 and lower layer 39, is shown positioned between foam blocks 41, 42. Upper layer 19 is attached at proximal end 53 to seat rest back end 37 inside inner compartment 33 just above zipper 32. Lower layer 39 is attached at proximal end 55 to seat rest back end 37 inside inner compartment 33 just below zipper 32. Seat inner pocket 38 can be closed by pocket closure hook and loop fasteners 43, 44 ( or other pocket closure means) at distal ends 54, 56 of upper and lower layers 19, 39, respectively. Pocket closure hook fastener 43 is attached to upper layer 19 at distal end 54;

accordingly, pocket closure loop fastener 44 is attached to lower layer 39 at distal end 56. Pocket closure hook and loop fasteners 43, 44 are positioned so that they mate with one another to close the distal end of inner pocket 38.

Inner pocket 38 is positioned and sized to contain heating pad 20 of the invention centrally in seat rest 23, where heating pad 20 is most effective in performing its therapeutic functions. Without inner pocket 38 to hold it in place, heating pad 20 could more easily shift positions to one side or to the front or back and, as a result, would not provide even heat to a user. Upper foam block 41 is thinner than lower foam block 42 to allow heat from heating pad 20 to more easily pass upwardly to a user yet still provide adequate cushioning for the user's comfort. Heating pad 20 can be removed from seat cushion 23 through the aperture created by opening zipper 32 and heated in a microwave oven prior to reinsertion into inner pocket 38 of seat rest 23. Returning to FIG. 6, inner pocket 38 is shown extending outwardly from seat rest 23, and heating pad 20 is shown removed from seat rest 23. Pocket closure hook and loop fasteners 43, 44 are shown disengaged to allow access through inner pocket 38 into inner compartment 33 of seat rest 23. Foam blocks 41, 42 can thus be removed from seat rest 23 for cleaning.

As also illustrated in FIG. 12, back rest 22 defines back rest foam compartment 52, which contains resilient, planar back rest foam block 31. Back rest 22 also includes a means for access, such as zipper 30, which is covered by flap 34, and which can be opened to remove foam block 31 from foam compartment 52 for cleaning. Handles 29, 29' are attached to seat rest back end 37, handle 29 attached above zipper 32 and handle 29' attached below zipper 32. A rear elevational view of heated seat cushion 21 is pictured in FIG. 7 with zippers 30 and 32 opened to allow access to back rest foam compartment 52 and seat rest inner compartment 33. Back rest foam block 31 is seen inside back rest foam compartment 52 of back rest 22. Heating pad 20 is shown inserted into inner pocket 38 between upper layer 19 and lower layer 39. Handle 29 is proximate the top half of zipper 32 and handle 29' is proximate the bottom half of zipper 32.

Figure 7:
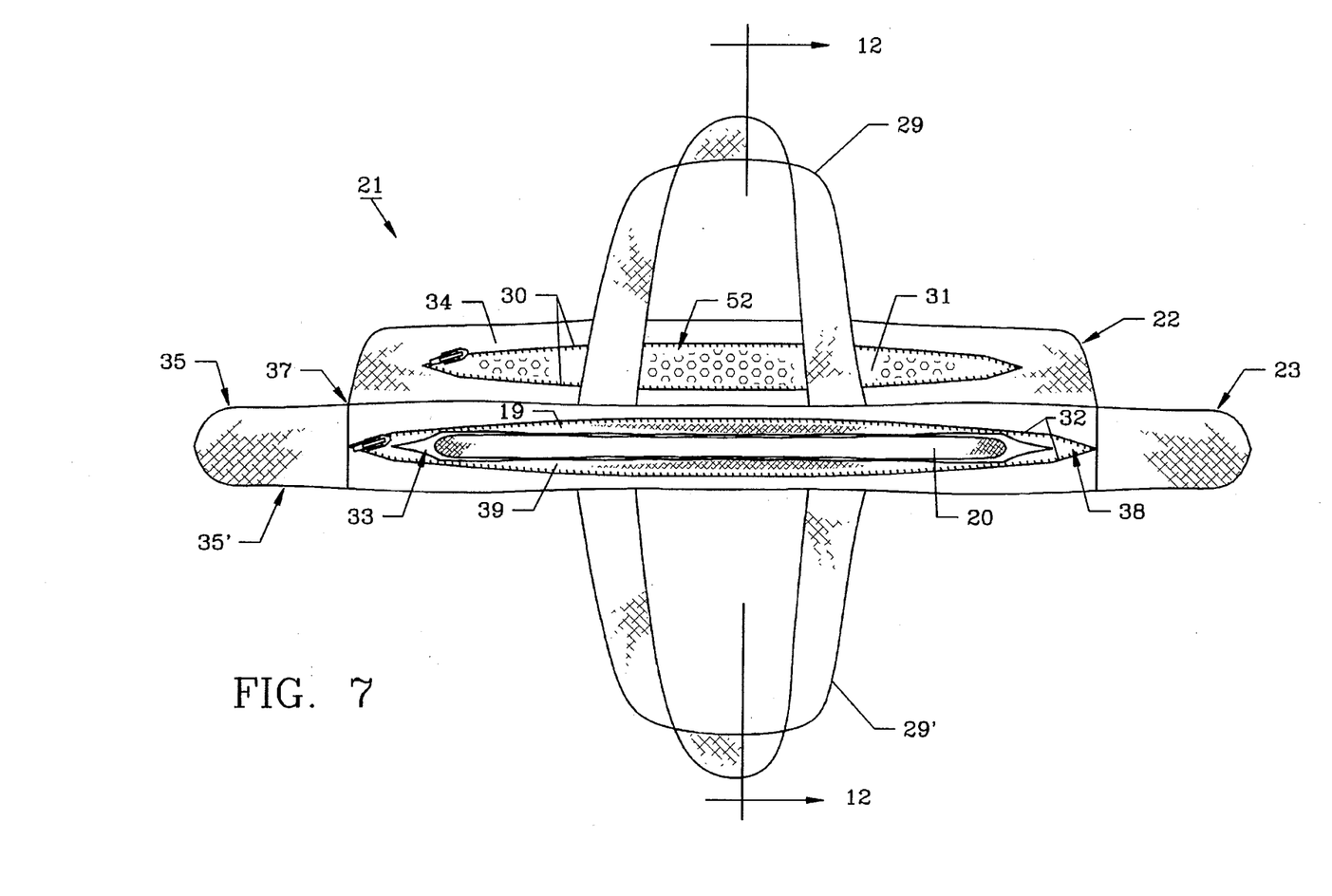
FIG. 7 illustrates a rear elevational view of the heated seat cushion depicted in FIG. 6, but with the back rest folded down and with the zippers opened to show the internal components of the heated seat cushion.

As previously stated, heating pad 20 can be removed from seat rest, placed in a microwave oven, heated to a desired temperature, and then reinserted into inner pocket 38. Heated seat cushion 21 can then be folded, latched with seat cushion closure hook and loop fasteners 28, 28' on front pouch 24 and back rest 22, and carried to a ball game or other event taking place in cold weather. Upon arrival at a chosen site, heated seat cushion 21 can be opened and placed on a bench seat or the like. A user can then sit on unfolded heated seat cushion 21 and remain warm and comfortable through several hours of outside activity. Upon leaving, the user can refold heated seat cushion 21 by reattaching seat cushion closure hook and loop fasteners 28, 28' and then easily transport heated seat cushion 21 back to his home or other destination.

Figure 13:
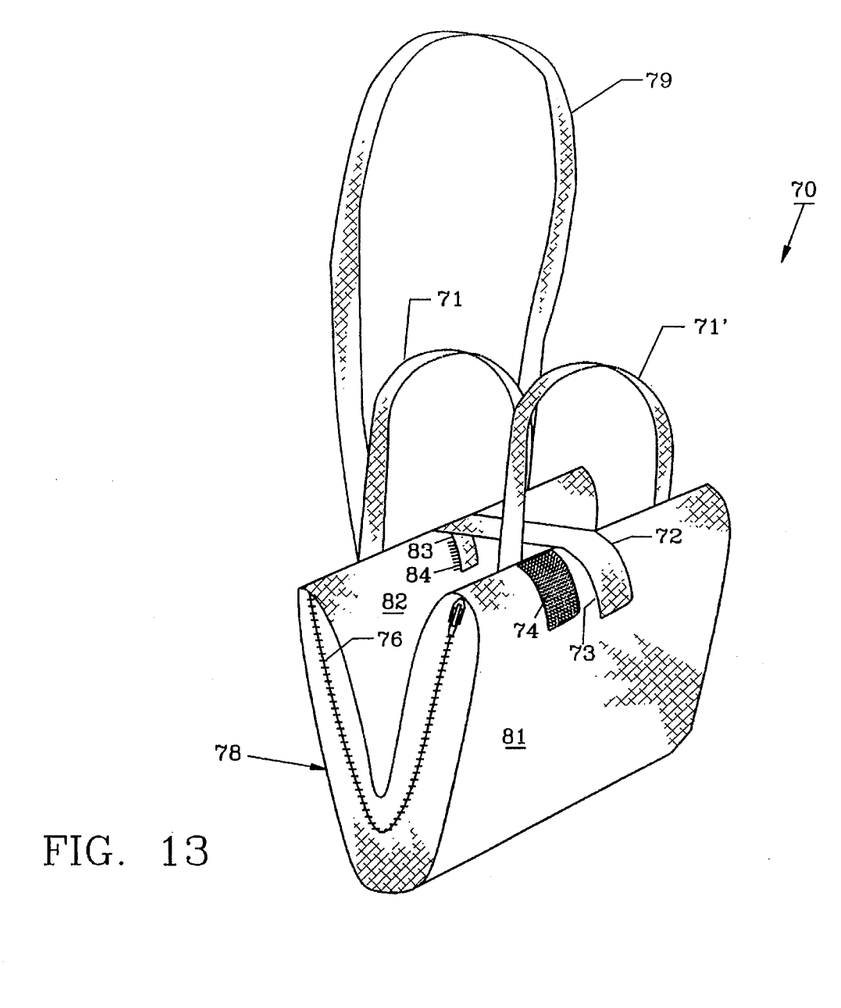
FIG. 13 depicts a perspective view of a folded alternate embodiment of the heated seat cushion having a removable heating pad and a shoulder strap.
Figure 14:
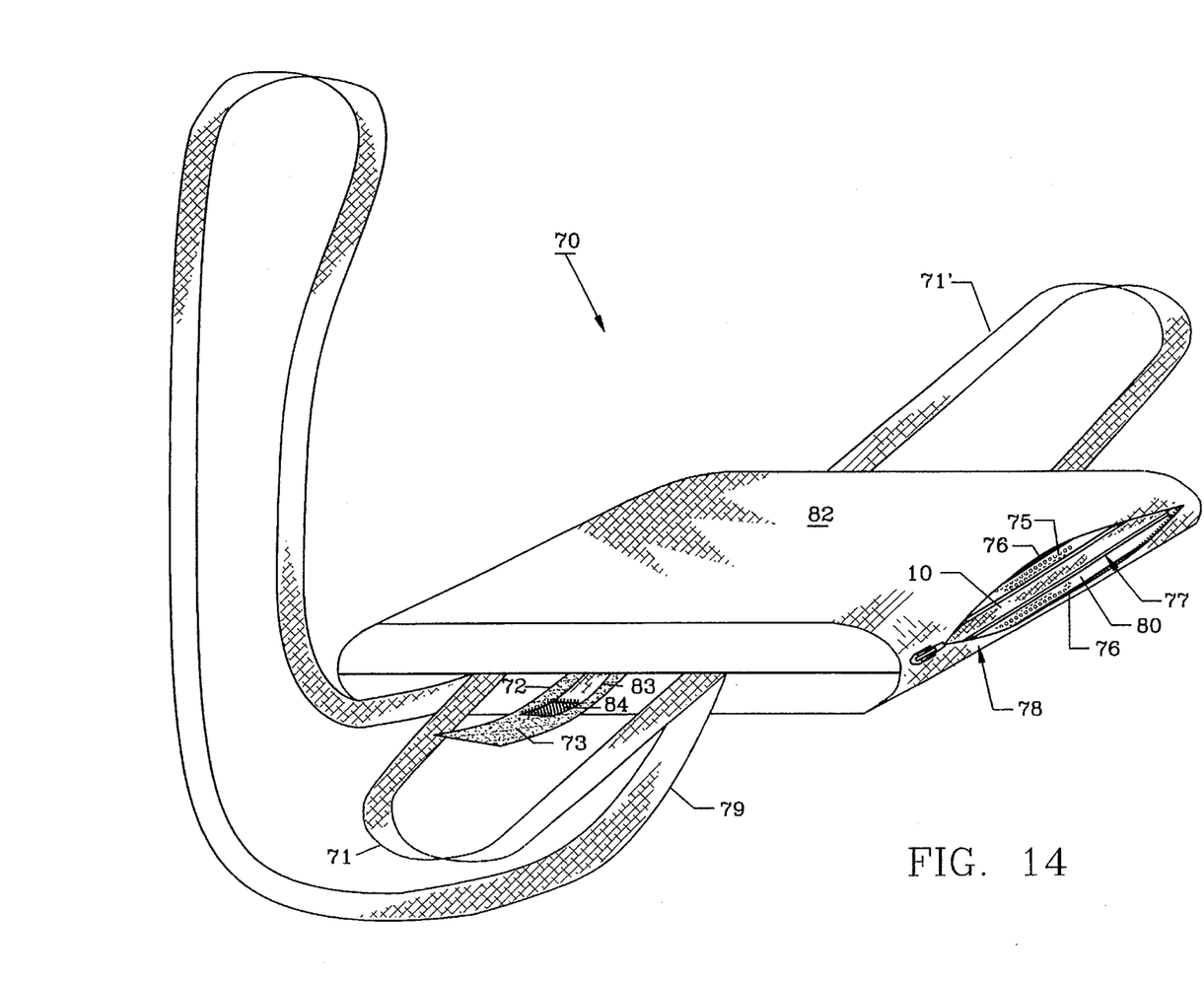
FIG. 14 shows the heated seat cushion of FIG. 13 in perspective view and unfolded.

In FIGS. 13 and 14, another embodiment of heated seat cushion 70 is shown having top cover layer 82 and bottom cover layer 81 made of durable fabric or other suitable material. Heated seat cushion 70 also includes handles 71, 71' attached to its sides and shoulder strap 79 attached to one side proximate handle 71. Means are provided to hold heated seat cushion 70 in a compact, folded configuration; for example, heated seat cushion 70 can be folded closed, as shown in FIG. 13, and latched with closure strap 72 having loop fastener 73 for engaging hook fastener 74, which is affixed on bottom cover layer 81 of seat cushion 70. Shoulder strap 79 can be folded and tucked out of the way using tab 83, which has distal end tab hook fastener 84 for engaging loop fastener 73 on closure strap 72 when tab 83 is looped around folded shoulder strap 79. Heated seat cushion 70 includes a means to open and close inner compartment 77 such as zipper 76 that extends horizontally along substantially the entire length of back end 78. Zipper 76 provides access to inner compartment 77, which houses upper foam block 75 and lower foam block 80. Heating pad 10 can be easily inserted and removed through opened zipper 76 and positioned between resilient foam blocks 75 and 80, as shown in FIG. 13.

The illustrations and examples provided herein are for explanatory purposes only and are not intended to limit the scope of the appended claims.

I claim:

1. A method of applying heat therapy to a person using a heated seat cushion containing a microwavable therapeutic pad within an insulated compartment, the method comprising the steps of:

(a) introducing a liquid and a liquid absorbing means into an envelope;

(b) applying a vacuum to said envelope to compress the contents thereof;

(c) sealing said envelope while said liquid absorbing means remains compressed to form a pad;

(d) subjecting said pad to microwave radiation;

(e) opening said insulated compartment;

(f) inserting the heated microwavable pad into the insulated compartment; and (g) sitting on the heated seat cushion to receive heat therefrom.

2. The method of claim 1 wherein the step of subjecting said pad to microwave energy comprises the step of subjecting said pad to microwave energy for approximately five minutes.

3. A method of applying heat therapy to a person using a heated seat cushion containing a microwavable therapeutic pad within an insulated compartment, the method comprising the steps of:

(a) introducing a liquid and a liquid absorbing means into an envelope;

(b) applying a vacuum to said envelope to compress the contents thereof;

(c) sealing said envelope while said liquid absorbing means remains compressed to form a pad;

(d) inserting the pad into the insulated compartment of the seat cushion;

(e) subjecting said seat cushion to microwave radiation; and (f) sitting on the heated seat cushion to receive heat therefrom.

4. A method of applying heat to a person using a heated seat cushion containing a microwavable pad within a compartment, the method comprising the steps of:

(a) introducing a liquid and a liquid absorbing means into an envelope;

(b) applying a vacuum to said envelope to compress the contents thereof;

(c) sealing said envelope while said liquid absorbing means remains compressed to form a pad;

(d) subjecting said pad to microwave radiation;

(e) inserting the heated microwavable pad into the seat cushion compartment; and (f) sitting on the heated seat cushion to receive heat therefrom.

5. A method of applying heat to a person using a heated seat cushion containing a microwavable pad within a compartment, the method comprising the steps of:

(a) introducing a liquid and a liquid absorbing means into an envelope;

(b) applying a vacuum to said envelope to compress the contents thereof;

(c) sealing said envelope while said liquid absorbing means remains compressed to form a pad;

(d) inserting the pad into the compartment of the seat cushion;

(e) subjecting said seat cushion to microwave radiation; and (f) sitting on the heated seat cushion to receive heat therefrom.

6. A seat cushion, comprising:

(a) a seat rest, said seat rest defining a compartment therein;

(b) a resilient top insulating member and a resilient bottom insulating member, said resilient top insulating member and said resilient bottom insulating member removably positioned within said compartment, said seat rest defining a seat rest opening, said seat rest opening in communication with said compartment to allow insertion and removal of said resilient top and said resilient bottom insulating members;

(c) a liquid filled therapeutic pad, said liquid filled therapeutic pad positionable within said compartment between said top and said bottom insulating members; and (d) a back rest, said back rest defining a foam block compartment therein, said foam block compartment containing a resilient foam block, said back rest hingedly joined to said seat rest proximate said seat rest opening, said back rest defining an opening, said opening in communication with said foam block compartment to allow insertion, and removal of said resilient foam block.

7. The seat cushion of claim 6, wherein said resilient top insulating member has a thickness approximately half the thickness of said resilient bottom insulating member.

8. The seat cushion of claim 6, wherein said back rest has a proximal end and a distal end, said proximal end of said back rest joined to said seat rest.

9. The seat cushion of claim 8, further comprising means to close said foam block compartment, said closing means located at said proximal end of said back rest.

10. The seat cushion of claim 9, wherein said closing means comprises a zipper.

11. The seat cushion of claim 6, wherein said seat rest has a proximal end and a distal end, said proximal end of said seat rest joined to said back rest.

12. The seat cushion of claim 11, further comprising means to close said seat rest opening, said closing means located at said proximal end of said seat rest.

13. The seat cushion of claim 12, wherein said closing means comprises a zipper.

14. The seat cushion of claim 11, further comprising a front pouch, said front pouch attached to said distal end of said seat rest, said front pouch defining an opening.

15. The seat cushion of claim 14, further comprising means to close said front pouch opening, said closing means located on said front pouch.

16. The seat cushion of claim 15, wherein said closing means comprises a hook-and-loop fastener.

17. The seat cushion of claim 11, further comprising a carrying handle, said handle attached to said proximal end of said seat rest.

18. The seat cushion of claim 11, further comprising a carrying strap, said strap attached to said proximal end of said seat rest.

19. The seat cushion of claim 6, further comprising an upper layer and a lower layer, said upper and lower layers having generally a rectangular shape, said upper and lower layers joined at their periphery along two opposing sides, said upper and lower layers positionable within said compartment, one end of said upper layer joined to said seat rest proximate said seat rest opening, one end of said lower layer joined to said seat rest proximate said seat rest opening opposite said upper layer, said upper and lower layers defining a pocket therebetween for reception of said liquid filled therapeutic pad.

20. The seat cushion of claim 19, further comprising hook-and-loop fasteners, said hook-and-loop fasteners opposingly attached to said upper and lower layers.

21. The seat cushion of claim 6, further comprising an upper layer and a lower layer, said upper and lower layers having generally a rectangular shape, said upper and lower layers joined at their periphery along two opposing sides, said upper and lower layers positionable within said compartment, one end of said upper layer joined to said seat rest proximate said seat rest opening, one end of said lower layer joined to said seat rest proximate said seat rest opening opposite said upper layer, said upper and lower layers defining a pocket therebetween for reception of said liquid filled therapeutic pad, a plurality of hook-and-loop fasteners, said hook-and-loop fasteners opposingly attached to said upper and lower layers.

* * * * *